United States Patent [19]

Bastiaans

[11] Patent Number: 4,735,906
[45] Date of Patent: Apr. 5, 1988

[54] SENSOR HAVING PIEZOELECTRIC CRYSTAL FOR MICROGRAVIMETRIC IMMUNOASSAYS

[75] Inventor: Glenn J. Bastiaans, College Station, Tex.

[73] Assignee: Texas A&M University

[21] Appl. No.: 675,524

[22] Filed: Nov. 28, 1984

[51] Int. Cl.$^4$ .................... G01N 33/53; H01L 41/00
[52] U.S. Cl. .................................... 436/527; 324/71.1; 367/157; 436/501; 436/518; 436/806
[58] Field of Search ............... 436/806, 501, 518, 527; 367/157; 324/71.1

[56] References Cited

U.S. PATENT DOCUMENTS

| | | | |
|---|---|---|---|
| 3,164,004 | 1/1965 | King . | |
| 3,863,495 | 2/1975 | Schulz et al. . | |
| 4,055,072 | 10/1977 | Fletcher et al. . | |
| 4,210,722 | 7/1980 | Silver | 435/176 |
| 4,236,893 | 12/1980 | Rice | 23/230 |
| 4,242,096 | 12/1980 | Oliveira et al. | 23/230 |
| 4,246,344 | 1/1981 | Silver, III | 435/39 |
| 4,312,228 | 1/1982 | Wohltjen | 73/597 |
| 4,314,821 | 2/1982 | Rice | 23/230 |
| 4,361,026 | 11/1982 | Muller et al. | 73/23 |

OTHER PUBLICATIONS

J. E. Roederer and Glenn J. Bastiaans, "Microgravimetric Immunoassay with Piezoelectric Crystals", 55 *Anal. Chem.* 2333-2336 (Dec. 1983).

J. R. Sportsman et al., "Chromatographic Properties of Silica-Immobilized Antibodies", 52 *Anal. Chem.*, 2013-2018 (1980).

A Shons et al., "An Immunospecific Microbalance", 6 *J. Biomed. Mater. Res.*, 565-570 (1972).

Konash & Bastiaans, "Piezoelectric Crystals as Detectors in Liquid Chromatography", 1929-1931 (1980).

*Primary Examiner*—Sidney Marantz
*Attorney, Agent, or Firm*—Arnold, White & Durkee

[57] ABSTRACT

A sensor and method for performing immunoassays using surface acoustic waves on a piezoelectric crystal is provided. A specific antigen or antibody is bonded to the surface of the piezoelectric crystal and its resonant frequency in a blank solution is determined. The sensor is then exposed to a test solution containing an antigen or antibody corresponding to the substance bonded to the surface of the crystal. As the antigen and antibody react, the resonant frequency of the crystal is altered. This change can be correlated to determine the amount of antigen or antibody in the test solution. A nonreactive reference sensor can also be used to compensate for any nonselective adsorption.

18 Claims, 2 Drawing Sheets

SENSOR HAVING PIEZOELECTRIC CRYSTAL FOR MICROGRAVIMETRIC IMMUNOASSAYS

BACKGROUND OF THE INVENTION

The present invention relates to apparatus and methods for performing immunoassays. More particularly, the invention relates to apparatus and methods for performing immunoassays using surface acoustic waves on a sensor.

Generally, the term "antigen" is applied to any foreign substance which, when present in a host animal, will stimulate the production of specific antibodies. These antibodies show a remarkable ability to bind selectively the antigen which stimulated their production. This ability of the antibodies to discriminate between the antigens which stimulated their production and the numerous other compounds having a similar structure is the basis for virtually all immunoassay techniques. These techniques are based on the principal that an antibody will form a complex by selectively binding with the antigen which stimulated its production.

Numerous different immunoassays are known in the art for the qualitative and quantitative determination of antigens and antibodies. Immunoassay procedures such as radioimmunoassay and fluoroimmunoassay are the most widely used methods in immunochemistry. Despite their great utility in the analysis of materials of clinical and biomedical importance, these methods are limited by the hazards and short lifetimes of radioactive labels, expensive instrumentation, complicated procedures and relatively long incubation periods. Although sensitivities obtained by radioimmunoassays are high, alternative techniques are being developed to overcome the need for radioactive labels. These include enzyme linked immunosorbant assays (ELISA) and recent advances in fluoroimmunoassays as well as the use of ion-selective electrodes for clinical applications. However, these techniques suffer from the disadvantages of requiring chemical modification of the antigen, highly specialized antisera, very precise timing during the assay and reagent instability. Because of the problems associated with these methods of performing immunoassays, efforts have been made to develop new, simpler techniques and procedures.

One area which has shown some promise in providing a new procedure is the use of piezoelectric oscillators for detecting antigens and antibodies. Various types of methods and sensors have been developed. For example, U.S. Pat. No. 4,242,096 discloses an indirect method for determining an antigen in a liquid sample. In this procedure, a piezoelectric oscillator is coated with the antigen which is to be determined. The antigen-coated oscillator is then contacted with the liquid sample and a predetermined amount of an antibody specific for the antigen being determined. This antibody then reacts with the antigen on the sensor and the antigen in the test solution. After the reaction is completed, the sensor is removed and the change in its resonant frequency because of the antibody is determined. The amount of antigen in the solution can then be determined by comparing this change in frequency to a standard curve.

Another sensor and method is disclosed in U.S. Pat. Nos. 4,236,893 and 4,314,821. In this method, an antigen specific for the antibody to be determined is bound to the surface of a piezoelectric oscillator. The antigen-coated oscillator is then exposed to a solution containing an unknown amount of the antibody. After the antibody in the solution has attached to the antigen on the oscillator, the oscillator is exposed to a substance which selectively binds to a specific subclass of the antibody being determined. This substance is referred to as a sandwiching substance. The frequency of the oscillator is measured before and after exposure to the sandwiching substance. The change in frequency is related to the amount of the subclass of antibody bound to the oscillator and the amount of the subclass of antibody in the solution can be quantified by reference to a standard curve.

While these sensors have provided a significant advancement in the art for performing immunoassays, they still have certain disadvantages. First, these sensors utilize bulk mode acoustic waves which propagate through the entire crystal thickness from one surface to an opposing surface. Additionally, these sensors were designed such that they could only oscillate when a gas was present at the crystal surface and close control of temperature and humidity was maintained. Further, these sensors can generally only be utilized to perform a single immunoassay.

Accordingly, it would be a significant advancement in the art to provide a sensor and method for performing immunoassays in which the sensor could be utilized for repeated measurements. It would be a further advancement if the sensor could determine the amount of antigen or antibody present while still in solution, thus eliminating the need to dry the oscillator and carefully control the temperature and humidity. Such a sensor and method are disclosed and claimed herein.

BRIEF SUMMARY OF THE INVENTION

In a preferred embodiment of the present invention, a pair of piezoelectric crystal sensors are used to detect and measure the amount of an antigen or antibody in a test solution. One sensor serves as a reference sensor and the other serves as an indicating sensor. Surface acoustic waves are generated on the surfaces of the crystals and changes in the resonant frequencies of the crystals as they interact with the test solution provide a means for determining the amount of test substance in the solution. The piezoelectric crystal in the indicating sensor is prepared by chemically bonding an antigen or antibody to the surface of the crystal. The surface of the crystal is first modified by bonding a monomer layer of a silane derivative to the quartz surface. The initial silane layer is polymerized with other silane derivatives to form a siloxane polymer having a high reactivity to proteins and the antigen or antibody is bound to this polymer. In a preferred embodiment, a silane-epoxy compound, glycidoxypropyltrimethoxysilane (GOPS), is deposited and polymerized on the surface of the sensor and the epoxy ring is hydrolyzed. After hydrolysis, carbonyldiimidazole is attached to the hydroxy groups. The antigen or antibody is then immobilized on the carbonyldiimidazole through amide linkages.

The reference sensor is prepared similar to the first, except that constituents which are nonreactive with the substance to be detected are attached to the hydrolyzed GOPS instead of an antigen or antibody.

The reference and indicator crystals are then placed in separate electronic oscillator circuits and their resonant frequencies using surface acoustic waves are measured in a blank solution and are ratioed. The sensors are then placed in a test solution containing the antigen or antibody to be determined. As the antigen or antibody binds with its counterpart on the surface of the indicator crystal, the vibrational resonant frequency of the crystal is altered. The change in the ratio of the indicator and reference frequencies before and after exposure to the test solution can then be compared against a reference chart to determine the amount of antigen or antibody in the test solution.

After an analysis has been performed, the sensor can be cleaned by rinsing with a solution capable of disrupting the antigen-antibody complex and can be reused inasmuch as the antigen or antibody is chemically bonded to the surface of the sensor.

DETAILED DESCRIPTION OF THE PREFERRED EMBODIMENT

The present invention provides a sensor and method for performing immunoassays. As used herein, immunoassays include any test involving antibodies, such antibodies for biomacromolecules (i.e., proteins, hormones, and nucleic acids) viruses, cells, bacteria, drugs, toxins, and complexed metal ions. Preferably, monoclinal antibodies are used.

The surface of a piezoelectric quartz crystal is prepared and an antigen or antibody is chemically bonded to the surface thereof. When this crystal is exposed to a test solution containing a corresponding substance selectively reactive with the antigen or antibody bonded to the surface of the crystal, the antigen and antibody form a complex and the change in the surface mass of the crystal causes a change in the resonant frequency. This change in the resonant frequency can be detected and can be utilized to determine the amount of substance in the test solution.

Figure 1:
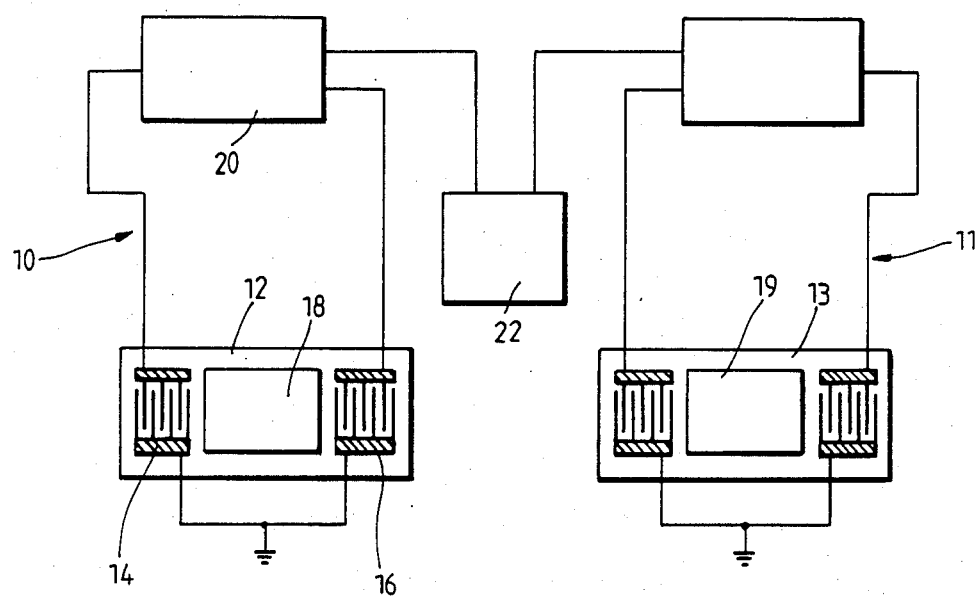
FIG. 1 is a schematic view of a sensor according to the present invention.

Reference is next made to FIG. 1 which illustrates a preferred embodiment of the present invention. A microgravimetric sensor generally designated at 10 is schematically illustrated and includes a piezoelectric crystal 12 for generating surface acoustic waves. In a preferred embodiment, the crystal is a quartz ST-cut surface acoustic wave device such as is manufactured and supplied by Valpey-Fisher of Hopkington, Massachusetts. It will be appreciated by those skilled in the art that other types of piezoelectric materials can also be used for crystal 12.

Electrodes 14 and 16 are provided on crystal 12 for generating and detecting the surface acoustic waves. The electrodes can be applied by any one of a number of means well known to those skilled in the art such as by vacuum deposition. In a preferred embodiment, the electrodes are constructed of interdigitized nickel transducers which are designed to yield a crystal resonant frequency of about 10.3 MHz in the circuit.

A sensing region 18 is formed in the center of the crystal 12 between electrodes 14 and 16. As more fully discussed hereinafter, sensing region 18 is designed to interact with the substance to be detected in the test solution and this interaction causes a change in the resonant frequency of crystal 12.

A wave generator 20 which includes a high gain RF amplifier is connected to electrodes 14 and 16 to create a delay line oscillator. Other methods of creating surface acoustic wave oscillators are disclosed in U.S. Pat. No. 4,361,026 incorporated herein by reference, and can also be utilized in the present invention.

A frequency/ratio meter 22 is included in the circuit to measure the resonant frequency of crystal 12. Frequency/ratio meter 22 can be any one of a number of monitoring devices such as a Hewlett-Packard 5328A Universal Counter.

The sensing region 18 in the center of crystal 12 is designed to be selectively reactive with the material to be measured by sensor 10. When performing immunoassays, an antigen or antibody corresponding to the antigen or antibody to be detected is included within sensing region 18. In a preferred embodiment, the antigen or antibody is chemically bonded to the crystal 12 with a alkoxy-organosilane. For example, a thin layer of glycidoxy-propyltrimethoxysilane (GOPS) is formed on the surface of crystal 12 as the base layer of sensing region 18. Preferably, the sensing region 18 is very thin, being only a few monolayers in thickness. The polymeric coating is preferably produced on the sensor surface by actually forming the polymer by reactions taking place at the sensor surface. This can be accomplished by subjecting the surface to alternate aqueous and nonaqueous treatments involving a silane derivative such as GOPS.

The polymer coating is then treated such that it can bind an antigen or antibody. In a first preferred embodiment, the GOPS is prehydrolyzed and once applied, the organic functional end of the GOPS is subjected to quantitative periodate oxidation to form an aldehyde to which the antibody or antigen can be attached. The attachment procedure involves incubation with the antigen or antibody followed by reduction of the amine bond formed during incubation to an amine bond with sodium borohydride. In a second preferred embodiment, the GOPS is hydrolyzed such that the epoxy rings are converted to hydroxy groups. After hydrolysis, carbonyldiimidazole is attached to the hydroxy groups. The carbonyldiimidazole will then immobilize antigens and antibodies through amide linkages. Because the antigen and antibodies are chemically bonded to the sensing region 18, the crystal 12 can be cleaned after a measurement has been made and can be reused.

Alternative methods of treating the sensor surface to bind the antigen or antibody include formation of other polymeric films which are effective for protein immobilization such as modified polyacrylamide polymers. The polymer preferably exhibits minimal nonselective adsorption. Thus, other compounds in the test solution do not adhere to the surface of the crystal sensor so as to effect the resonant frequency.

In the preferred embodiment, a second sensor 11 is provided. This sensor includes a piezoelectric crystal 13 which is also used for generating surface acoustic waves. Sensor 11 is essentially identical to sensor 10 except that sensing region 19 on sensor 11 is prepared to be generally unreactive with any of the substances in the test solution as discussed more fully hereinafter. This allows the system to compensate for temperature changes and any nonselective adsorption which might occur at the sensor surface.

Figure 2:
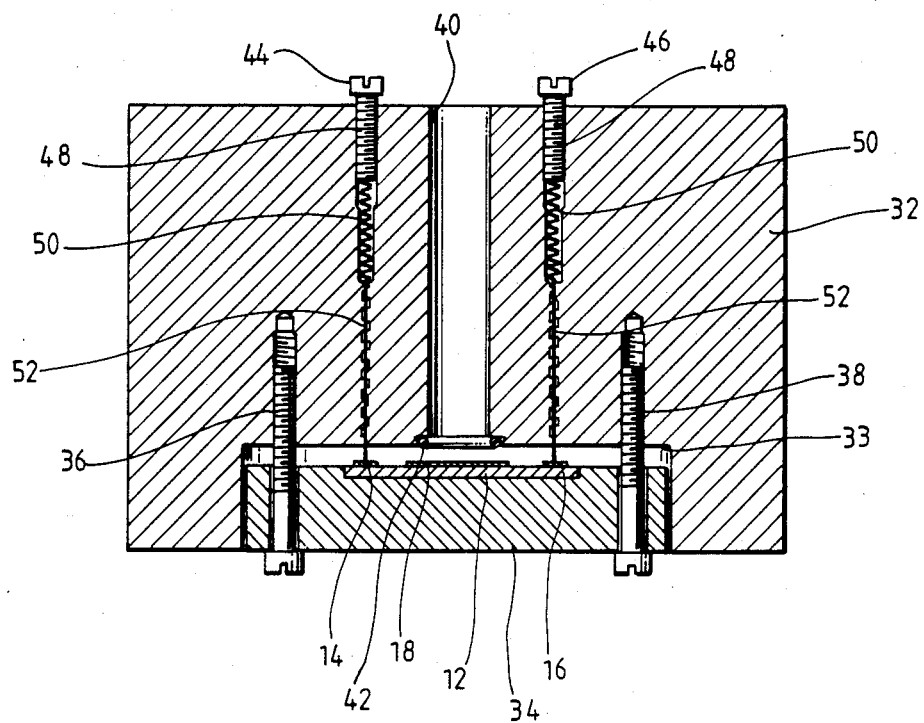
FIG. 2 is a partially exploded cross-sectional view of a detector cell having a sensor included therein.

Reference is next made to FIG. 2 which illustrates a detector cell 30 which can be used for performing measurements utilizing the present invention. Detector cell 30 includes a body 32 having a chamber 33 formed in the bottom thereof. A positioning insert 34 fits within chamber 33 and holds crystal 12 in cell 30. Positioning insert 34 is held in place in block 32 by screws 36 and 38. A sample introduction well 40 is formed through body 32 such that it is in communication with chamber 33. Sensing region 18 on crystal 12 is positioned in the bottom of well 40. An O-ring 42 is positioned in the bottom of well 40 above crystal 12 to prevent leakage of the test solution from well 40 into chamber 33.

Electrical contact with electrodes 14 and 16 on crystal 12 is made through assemblies 44 and 46. Each of assemblies 44 and 46 includes a screw 48, a spring 50 and an electrode 52. In this embodiment, four needle-point electrodes (two on each side) are utilized for each crystal to maintain constant pressure against electrodes 14 and 16.

Figure 3:
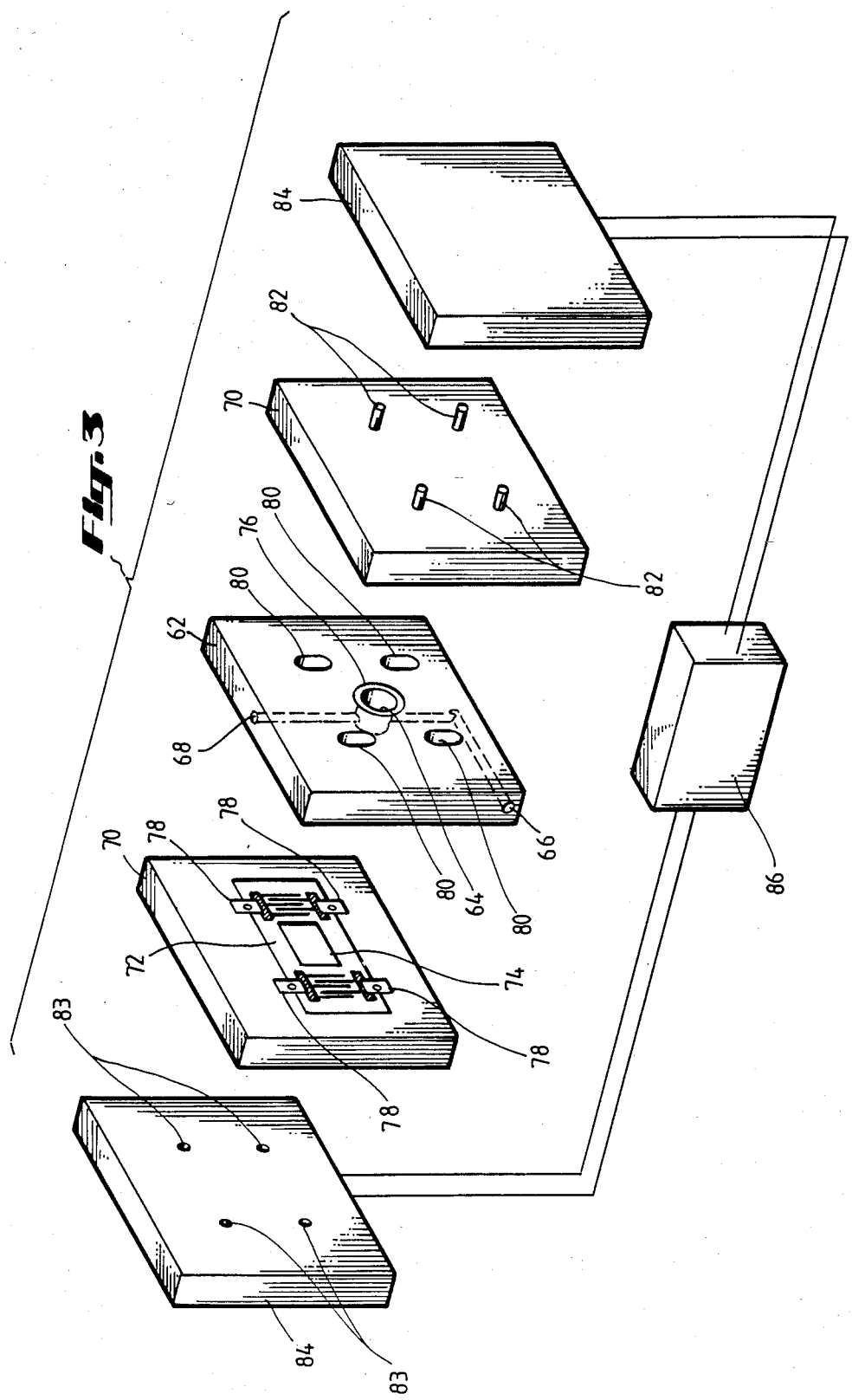
FIG. 3 is an exploded view of a second preferred embodiment of a detector cell incorporating the present invention.

Referring now to FIG. 3, a second preferred embodiment of a detector cell 60 is illustrated. Detector 60 includes a stop flow cell 62 having a cylindrical sample chamber 64 extending therethrough. An inlet port 66 and an outlet port 68 extend from the sides of flow cell 62 to chamber 64.

A crystal holder 70 is positioned on each side of stop flow cell 62. Holders 70 support piezoelectric crystals 72 such that sensing region 74 on crystals 72 is adjacent to the ends of sample chamber 64. An O-ring 76 is positioned in a countersunk annulus around the ends of chamber 64 to prevent the test solution from leaking out.

Crystals 72 are held on holders 70 by four toe clamps 78. Recesses 80 are formed in stop-flow cell 62 to coincide with toe clamps 78 when the detector 60 is assembled. Tip plugs 82 are connected to toe clamps 78 through holders 70. Plugs 82 connect the crystals through sockets 83 to electronic assemblies 84 which contain oscillators for the crystals. A frequency/ratio meter 86 is connected to electronic assemblies 84.

In performing immunoassays according to the present invention, two sensors are generally utilized. The first sensor is prepared as described above and includes an antibody or antigen bonded to the surface of the sensor. This sensor acts as an indicator sensor and reacts with the substance to be detected in the solution. The second sensor is a reference sensor which is used to compensate for changes in temperature of the solution and also to compensate for any nonselective bonding which may occur at the sensor surface. This reference sensor is prepared similar to the indicator sensor except that a nonreactive species is bonded to the crystal 12. Thus, sensing region 18 is treated to be generally unreactive with any of the substances which will be in the test solution. This can be accomplished by immobilizing a nonreactive antibody such as myeloma protein to the polymer. Other molecules which are nonreactive to the species being detected can also be used.

In performing an immunoassay, the resonant frequencies of surface acoustic waves generated in the indicator and reference sensors exposed to a blank solution are determined. These frequencies are then ratioed. The sensor surfaces are then exposed to a test solution containing the antigen or antibody to be detected. This can be accomplished in the detector cell as described above with respect to FIG. 2 or in a flow cell as described above with respect to FIG. 3. Other cell configurations will be apparent to those skilled in the art.

As the antigen or antibody in the test solution binds with the antigen or antibody bonded to the surface of the indicator crystal, the surface mass on the crystal increases which causes a change in the resonant frequency of the crystal. After an appropriate period of time has passed such that the reaction between the antigen and the antibody is substantially complete, the resonant frequencies of the indicator and reference sensors are again determined. These frequencies are then ratioed and compared to the ratio of the frequencies before the sensors were exposed to the test solution. The change in the ratio of resonant frequencies can then be compared against a standard chart to determine the amount of antigen or antibody present in the test solution. A standard chart can be prepared by exposing a pair of sensors to a series of solutions containing known amounts of the substance to be determined and by plotting the changes in the frequency ratios when the sensors are exposed to these solutions.

Because of the design of the sensor apparatus, the resonant frequencies of the crystals can be determined while the sensors are still in the solution. This feature provides a much simpler and faster sensing method than was available with prior art sensors. Additionally, because the antigen or antibody is chemically bonded to the sensor surface, the corresponding antigen or antibody can be removed after a test procedure has been completed such that the sensor can be reused. The substance which was detected can be removed from the sensor surface by washing the sensor with any solution which disrupts the antigen-antibody complex. For example, a high ionic strength solution such as a sodium chloride solution can be used.

The following examples are illustrative of various features of the invention and the types of tests which can be performed using the present invention.

EXAMPLE 1

A pair of ST-cut, 1 in.×0.5 in.×0.04 in. surface acoustic wave devices from Valpey-Fisher were used. Electrode patterns were applied via a vacuum deposition technique and were constructed of interdigitized nickel transducers designed to yield a crystal resonant frequency of 10.3 MHz.

The sensing region between the electrodes on each crystal was first etched with a HF/NaF/NH$_4$F.HF solution to increase surface area. The quartz substrate of the indicator sensor was treated with a solution containing 20 ml isopropanol, 2.5 ml water, 2.5 ml GOPS, and 1.0 ml acetic acid, which had been stirred for 1 hour. To convert the GOPS epoxy groups to aldehyde groups, the substrate was placed in a pH 2.5 acetate buffer containing 1 molar periodic acid. Goat antibody to human IgG was immobilized on the surface by exposing the surface to a solution of the protein in borate buffered saline at pH 8.5. After 24–36 hours of incubation, sodium borohydride was added to the protein solution in order to reduce the initial imine bonds to amine linkages. The reference crystal was modified to contain oxidized GOPS but no antibody.

The crystals were each placed in the feedback loop of high gain RF amplifiers. The crystal controlled frequencies and frequency ratios were monitored with a Hewlett-Packard 5328A universal counter.

Delrin holders as illustrated in FIG. 2 were constructed to achieve simultaneous electrical and sample contact with the indicator and reference crystals.

A blank solution of borate buffered saline was added to the sample well of each holder and the resonant frequencies were measured and ratioed. Solutions of borate-buffered saline containing IgG antigen were then added to both sample wells. The resonant frequencies were again determined and ratioed. The indicator sensor demonstrated a greater frequency shift thus indicating that specific absorption was occuring at the sensor surface. Different concentrations of IgG were tested and the results were plotted.

EXAMPLE 2

The procedure of Example 1 was repeated except that human blood serum diluted by a factor of 100 with BBS was used in place of the borate-buffered saline solution. Again, different concentrations of IgG were tested and the results were plotted. The results obtained using the blood serum were substantially the same as those obtained with the saline solution which indicates that the system is effective in biological fluids.

EXAMPLE 3

A ST-cut SAW device was prepared, and surface etched as described in Example 1. The quartz substrate was treated for 2 hours with a solution containing 20 ml isopropanol, 2.5 ml water, 2.5 ml GOPS, 0.25 ml triethylamine, and 1.0 ml acetic acid, which had been stirred for 1 hour. The substrate was then dried with acetone and placed in a solution of 20 ml dry toluene and 2.5 ml GOPS. The substrate was refluxed in the GOPS-toluence solution for 2 hours. The above aqueous and nonaqueous GOPS treatments were repeated.

The substrate was then placed in a pH 2.5 acetate buffer and stirred for 30 minutes in order to hydrolyze the GOPS epoxy groups. Following hydrolysis, the substrate was placed in a solution containing 20 ml dry acetone and 0.8 ml carbonyldiimidazole for 90 minutes so as to activate the GOPS siloxane polymer for bonding to protein. The activated substrate was incubated 24 to 36 hours with human IgG in pH 8.5 borate buffered saline (BBS) and then for 12 hours with 1 mg/ml glycine in BBS.

The sensor produced was found to selectively bind antibody to human IgG (anti-human IgG). This binding was detected by the observation of oscillator frequency shifts upon exposure to the antibody. Binding was confirmed by exposing the sensor to $^{125}$I radiolabeled antibody. Surface bound label was detected using nuclear counting techniques.

EXAMPLE 4

A ST-cut SAW device was prepared and surface etched as described in Example 1. It was then subjected to repeated aqueous and nonaqueous treatments of silane solution as described in Example 3 except that the silane was aminopropyltriethoxysilane (APS). The APS-polymer coated substrate was activated for protein immobilization by treatment with a solution containing 20 ml dry acetone and 10 g of diisocyanohexane for 90 minutes. The substrates were incubated with a pH 8.5 BBS solution containing human IgG for 24–36 hours and then with 1 mg/ml glycine/BBS solution for 12 hours.

The sensor produced selectively bound anti-human IgG. This binding was detected as described in Example 3.

EXAMPLE 5

A ST-cut SAW device was prepared, etched, treated with GOPS and oxidized as described in Example 1. Protein in the form of a polyclonal antibody against influenza virus A was immobilized on the surface by incubation with a pH 8.5 BBS solution of the antibody for 24–36 hours. The imine bond formed was reduced to an amine with sodium borohydride.

The sensor produced was exposed to influenza virus A while oscillating. Frequency shifts observed were proportional to the relative concentration of influenza virus present. These frequency shifts indicated influenza virus A was binding to the sensor surface in proportion to its solution concentration.

EXAMPLE 6

A ST-cut SAW device was prepared, etched, treated with GOPS, hydrolyzed, and activated as described in Example 3. A protein in the form of monoclonal anti-human IgG was immobilized by incubation in a pH 8.5 BBS solution for 24–36 hours.

The sensor produced was exposed to solutions of human IgG while oscillating. The shifts in resonant frequency observed were proportional to the concentration of human IgG, thus indicating that the sensor was surface binding IgG in proportion to its solution concentration.

As will be readily appreciated, the invention may be embodied in other specific forms without departing from its spirit or essential characteristics. For example, modified oscillator circuits can be used with the crystals. Also, with certain solutions it may be possible to perform measurements using only an indicator sensor. The described embodiments are thus to be considered in all respects only as illustrative and not restrictive. The scope of the invention is, therefore, indicated by the appended claims rather than by the foregoing description. All changes or modifications which come within the meaning and range of equivalency of the claims are to be embraced within their scope.

We claim:

1. A method for performing immunoassays, said method comprising the steps of:
   measuring in a blank solution the resonant frequency of a piezoelectric crystal having an antibody or antigen bonded to the surface thereof;
   exposing said antibody or antigen on said crystal to a test solution containing an antigen or antibody corresponding to said bonded antibody or antigen for a period such that the antigen can bind with the corresponding antibody so as to increase the mass on the surface of the crystal; and
   measuring in said test solution the resonant frequency of the piezoelectric crystal and determining the change in frequency.

2. A method for performing immunoassays as defined in claim 1, further comprising:
   measuring in a blank solution the resonant frequency of a reference piezoelectric crystal and ratioing said reference frequency with the frequency of the indicator crystal;
   exposing the reference crystal to the test solution; and
   measuring in said test solution the resonant frequency of the reference crystal after exposure and ratioing said frequency with the frequency of the indicator crystal.

3. A method for performing immunoassays as defined in claim 1, further comprising comparing the frequency change to a standard curve.

4. A method for performing immunoassays as defined in claim 1, wherein the resonant frequency is determined using surface acoustic waves.

5. A method for performing immunoassays as defined in claim 2, wherein the resonant frequencies are determined using surface acoustic waves.

6. A sensor for performing immunoassays comprising:
   an indicator piezoelectric crystal having a specific antigen or antibody bonded to a portion of the surface thereof;
   means for forming surface acoustic waves on said crystal such that said waves pass through said antigen or antibody; and
   means for determining the resonant frequency of the surface acoustic waves on said crystal.

7. A sensor for performing immunoassays as defined in claim 6, wherein said piezoelectric crystal is a quartz crystal.

8. A sensor for performing immunoassays as defined in claim 6, wherein said antigen or antibody is covalently bonded to the surface of said crystal.

9. A sensor for performing immunoassays as defined in claim 6, wherein said antigen or antibody is bonded to a thin polymer film formed on the surface of said crystal.

10. A sensor for performing immunoassays as defined in claim 9, wherein said polymer film is less than about 5 monolayers in thickness.

11. A sensor for performing immunoassays as defined in claim 9, wherein said polymer film is a siloxane polymer.

12. A sensor for performing immunoassays as defined in claim 9, wherein said polymer film is a modified polyacrylamide polymer.

13. A sensor for performing immunoassays as defined in claim 9, wherein said polymer film exhibits minimal nonspecific adsorption.

14. An apparatus for performing immunoassays comprising:
   a first indicator sensor comprising a piezoelectric crystal having a specific antigen or antibody bonded to a portion of the surface thereof;
   a reference sensor comprising a piezoelectric crystal adapted such that it is substantially nonreactive with antigens and antibodies;
   means for creating surface acoustic waves on said indicator sensor and said reference sensor; and
   means for measuring the resonant frequencies of said indicator sensor and said reference sensor.

15. A sensor as defined in claim 6 wherein said means for forming surface acoustic waves comprises a wave generator including a high gain RF amplifier.

16. A sensor as defined in claim 11 wherein the siloxane polymer is deposited by multiple bonding steps.

17. A sensor as defined in claim 16 wherein the multiple bonding steps comprise alternating aqueous and nonaqueous treatments.

18. An apparatus as defined in claim 14 wherein said sensors are positioned at the bottom of sample introduction wells.

* * * * *

UNITED STATES PATENT AND TRADEMARK OFFICE
CERTIFICATE OF CORRECTION

PATENT NO.    : 4,735,906
DATED         : April 5, 1988
INVENTOR(S)   : Glenn J. Bastiaans and Joy E. Roederer It is certified that error appears in the above-identified patent and that said Letters Patent are hereby corrected as shown below:

On the title page inventors should read

-- Inventor(s):   Glenn J. Bastiaans, College Station, Tex.
                  and Joy E. Roederer, Racine, Wisconsin --

Signed and Sealed this

Twenty-fifth Day of October, 1988

Attest:

DONALD J. QUIGG

Attesting Officer                    Commissioner of Patents and Trademarks